US009877911B2

(12) United States Patent
Groves et al.

(10) Patent No.: US 9,877,911 B2
(45) Date of Patent: Jan. 30, 2018

(54) NON-AQUEOUS ORAL CARE COMPOSITIONS

(75) Inventors: Brian Joseph Groves, Bebington (GB); Philip Christopher Waterfield, Bebington (GB)

(73) Assignee: Conopco, Inc., Englewood Cliffs, NJ (US)

( * ) Notice: Subject to any disclaimer, the term of this patent is extended or adjusted under 35 U.S.C. 154(b) by 360 days.

(21) Appl. No.: 13/704,108

(22) PCT Filed: Jun. 16, 2011

(86) PCT No.: PCT/EP2011/060003
§ 371 (c)(1),
(2), (4) Date: Dec. 13, 2012

(87) PCT Pub. No.: WO2011/160996
PCT Pub. Date: Dec. 29, 2011

(65) Prior Publication Data
US 2013/0095045 A1  Apr. 18, 2013

(30) Foreign Application Priority Data
Jun. 23, 2010 (EP) .................................. 10167070

(51) Int. Cl.
*A61Q 11/00* (2006.01)
*A61K 8/86* (2006.01)
*A61K 8/24* (2006.01)
*A61K 8/34* (2006.01)
*A61K 8/39* (2006.01)
*A61K 8/81* (2006.01)

(52) U.S. Cl.
CPC .................. *A61K 8/86* (2013.01); *A61K 8/24* (2013.01); *A61K 8/345* (2013.01); *A61K 8/39* (2013.01); *A61K 8/8147* (2013.01); *A61Q 11/00* (2013.01); *A61K 2800/31* (2013.01)

(58) Field of Classification Search
USPC ............................................. 424/49, 52, 57
See application file for complete search history.

(56) References Cited

U.S. PATENT DOCUMENTS

| 3,574,824 | A | | 4/1971 | Echeandia et al. |
| 4,837,008 | A | | 6/1989 | Rudy et al. |
| 5,256,402 | A | * | 10/1993 | Prencipe et al. ................. 424/53 |
| 5,424,060 | A | * | 6/1995 | Hauschild ........................ 424/52 |
| 5,718,886 | A | | 2/1998 | Pellico |
| 5,820,852 | A | * | 10/1998 | Burgess ................... A61K 8/19 424/49 |
| 2004/0047814 | A1 | * | 3/2004 | Xu et al. ......................... 424/49 |

FOREIGN PATENT DOCUMENTS

| DE | 102004020622 | | 12/2005 |
| DE | 102004020622 | A1 | 12/2005 |
| GB | 1332556 | A | 10/1973 |
| GB | 220141 | A | 1/1990 |
| WO | WO9603108 | A1 | 2/1996 |
| WO | WO2008068149 | A1 | 6/2008 |
| WO | WO2009076491 | A2 | 6/2009 |

OTHER PUBLICATIONS

Bonacucina et al., Rheological, adhesive and release characterisation of semi solid carbopol/tetraglycol systems, International Journal of Pharmaceutics, Jan. 13, 2006, pp. 129-140, vol. 307, No. 2.
PCT International Search Report in PCT application PCT/EP 2011/060003 dated Oct. 28, 2011 with Written Opinion.
European Search Report in EP application EP 10 16 7070 dated Jan. 20, 2011.

* cited by examiner

*Primary Examiner* — Lezah Roberts
(74) *Attorney, Agent, or Firm* — Greenberg Traurig, LLP

(57) ABSTRACT

The invention provides a non-aqueous oral care composition with a liquid continuous phase comprising a thickening agent, a humectant, and one or more liquid polyethylene glycols having a melting point below 25° C., in which the liquid continuous phase is structured with crystals of one or more solid polyethylene glycols having a melting point of 25° C. or above. The rheological behavior of the composition of the invention corresponds well with the characteristic rheological behavior of typical aqueous dentifrice formulations.

11 Claims, No Drawings

NON-AQUEOUS ORAL CARE COMPOSITIONS

FIELD OF THE INVENTION

The present invention is concerned with non-aqueous oral care compositions.

BACKGROUND OF THE INVENTION

Oral care compositions such as dentifrices typically contain dentally acceptable abrasive, humectant, water, and water-soluble polymer which serves as a thickener and binder for the ingredients. A variety of other ingredients such as flavours, sweeteners, preservatives and fluoride are also utilized at low levels.

However there are many materials which are physically or chemically incompatible with the aqueous environments found in typical dentifrice formulations.

Non-aqueous formulations have been suggested as a way of improving the stability of these materials. For example, WO96/03108 describes a non-aqueous dentifrice composition comprising a carboxyvinyl polymer, a humectant, a polyethylene glycol and a dentally acceptable abrasive. The carboxyvinyl polymer is stated to thicken the humectant materials and provide the necessary rheology in order to suspend any required abrasive material. A polyethylene glycol selected from PEG 300 and PEG 400 is stated to reduce stickiness from the formulation and give a smooth textured product.

A problem with non-aqueous formulations such as those disclosed in WO96/03108 is that they do not behave rheologically like a typical aqueous dentifrice. This problem is observed both during manufacture and during use by the consumer. It has led to manufacturing difficulties and reduced acceptance amongst consumers. Viscosity profile and flow characteristics are key factors governing ease of processing, product performance and consumer perception of a dentifrice.

The present inventors have found that this problem can be solved by the incorporation of a particular combination of polyethylene glycols.

SUMMARY OF THE INVENTION

The present invention provides a non-aqueous oral care composition with a liquid continuous phase comprising a thickening agent, a humectant, and one or more liquid polyethylene glycols having a melting point below 25° C., in which the liquid continuous phase is structured with crystals of one or more solid polyethylene glycols having a melting point of 25° C. or above.

The rheological behaviour of the composition of the invention corresponds well with the characteristic rheological behaviour of typical aqueous dentifrice formulations. This correspondence is observed across a wide range of conditions of temperature and shear. Compared to previous non-aqueous dentifrice formulations, the composition of the invention has improved microstructure, ease of processing and excellent sensory properties.

A particular advantage of the composition of the invention is its thermal storage stability across an extended range of temperature. Contrary to what has been observed in previous anhydrous dentifrice formulations, the composition of the invention remains fully stable and functional at temperatures as low as 5° C. and as high as 50° C.

DETAILED DESCRIPTION OF THE INVENTION

The composition of the invention is non-aqueous. By "non-aqueous" it is generally meant that water is not deliberately added to the composition in any significant quantity. However, the term "non-aqueous" does not mean that small amounts of water cannot be present, for example as a consequence of its association with hygroscopic raw materials. Accordingly, for the purposes of this invention, the term "non-aqueous" generally means that water is present in an amount no greater than about 5%, more preferably no greater than about 3% by weight based on the total weight of the composition.

Thickening Agent

The liquid continuous phase of the composition of the invention comprises a thickening agent. The thickening agent helps to impart a desirable viscosity profile and desirable flow characteristics to the composition.

Suitable thickening agents for use in the invention are those which are operable in non-aqueous systems. Examples of such materials include organic macromolecules which do not necessarily require hydration with water in order to build viscosity, but can also build viscosity by alternative mechanisms such as by hydrogen bonding in the presence of hydroxyl donors such as polyols. Carboxyvinyl polymers have been found to be useful in this context. Preferred carboxyvinyl polymers for use in the invention have a molecular weight of at least about 750,000, more preferably at least about 1,250,000, most preferably at least about 3,000,000 g/mol. A suitable chemical class of such carboxyvinyl polymers for use in the invention includes cross-linked polymers having a polymer backbone derived from acrylic acid, substituted acrylic acid, or salts or esters thereof, in which the crosslinking agent contains two or more carbon-carbon double bonds and is derived from a polyhydric alcohol. Specific examples of such materials are homopolymers of acrylic acid cross-linked with allyl ethers of sucrose or pentaerythritol and homopolymers of acrylic acid cross-linked with divinyl glycol. The most preferred carboxyvinyl polymer for use in the compositions of the present invention is a homopolymer of acrylic acid cross-linked with allyl ethers of pentaerythritol, which is slightly pre-neutralised (1 to 3%) by potassium salt. This pre-neutralisation is done in order to precipitate polyacrylic acid in the presence of the polymerisation solvent. Such a material is commercially available, for example, as CARBOPOL® 974P NF Polymer, ex Lubrizol Advanced Materials, Inc. Mixtures of any of the above described materials may also be used.

The level of thickening agent will depend on the particular type chosen, but generally ranges from 0.05 to 10% by total weight thickener based on the total weight of the composition. When the thickening agent is a carboxyvinyl polymer (as described above), the amount of carboxyvinyl polymer in compositions of the invention suitably ranges from 0.05 to 5%, preferably from 0.1 to 2%, more preferably from 0.2 to 0.5% by total weight carboxyvinyl polymer based on the total weight of the composition.

Humectant

The liquid continuous phase of the composition of the invention comprises a humectant. The humectant helps to keep the composition from hardening or crystallizing upon exposure to air. It also helps to give the composition a moist feel to the mouth, and may in some cases impart a desirable sweetness.

Preferred humectants for use in the invention include organic polyols having 3 or more hydroxyl groups in the molecule (hereinafter termed "organic polyols"). Examples of such materials include glycerol, sorbitol, xylitol, mannitol, lactitol, maltitol, erythritol, and hydrogenated partially hydrolyzed polysaccharides. The most preferred organic polyol is glycerol. Mixtures of any of the above described materials may also be used.

The level of humectant will depend on the particular type chosen, but generally ranges from about 20 to 90% by weight based on the total weight of the composition. When the humectant is one or more organic polyols (as described above), the amount of organic polyol suitably ranges from 35 to 75%, more preferably from 45 to 70% by total weight organic polyol based on the total weight of the composition. Most preferably the composition of the invention is organic polyol-based. In the context of the present invention, the term "organic polyol-based" means that the composition is not oil-based or water-based, but instead, organic polyols (as defined above) are a principal component in the composition. By "principal component" is meant that the organic polyols (as defined above) when taken together, make up a higher portion of the composition's weight than any other compound. Ideally the composition of the invention is glycerol-based (i.e. glycerol makes up a higher portion of the composition's weight than any other compound) and contains from 45 to 70% by weight glycerol based on the total weight of the composition.

Solid Polyethylene Glycol

The liquid continuous phase of the composition of the invention is structured with crystals of one or more solid polyethylene glycols having a melting point of 25° C. or above. Preferably the melting point ranges from 35 to 65° C., more preferably from 55 to 60° C.

The crystals of the solid polyethylene glycol(s) help to provide an optimised microstructure for the composition.

Polyethylene glycols have the general formula $H(OCH_2CH_2)_n$ OH, where n is the number of repeating oxyethylene units. Commercially available polyethylene glycols are usually not uniform chemical compounds, but instead consist of a distribution of similar polymer members of the homologous polyethylene glycol series, defined by average values of n and molecular weight. The melting point generally increases with increasing average values of n and molecular weight. Suitable solid polyethylene glycols have an average value of n in the above general formula ranging from about 20 to 220, preferably from about 40 to 150, more preferably from about 32 to 90, most preferably from about 60 to 75. The average molecular weight suitably ranges from about 950 to 11,250, preferably from about 1800 to 6600, more preferably from about 1400 to 4400, most preferably from about 2700 to 3700 g/mol. Suitable commercially available materials include for example Polyglykol® 3000 (ex Clariant). Mixtures of any of the above described materials may also be used.

The amount of solid polyethylene glycol (as defined above) in compositions of the invention suitably ranges from 0.1 to 5%, preferably from 0.5 to 3%, more preferably from 1 to 2.5% by total weight solid polyethylene glycol (as defined above) based on the total weight of the composition.

Liquid Polyethylene Glycol

The liquid continuous phase of the composition of the invention one or more liquid polyethylene glycols having a melting point below 25° C. Preferably the melting point ranges from −50 to 22° C., more preferably from −15 to 8° C., most preferably from 4 to 8° C.

The liquid polyethylene glycol(s) helps to make processing of the composition easier, especially at high shear, by reducing the overall viscosity of the liquid continuous phase.

Preferred liquid polyethylene glycols have an average value of n in the general formula $H(OCH_2CH_2)_n$ OH (as described above) ranging from about 4 to 12, more preferably about 6 to 8, most preferably about 8. The average molecular weight suitably ranges from about 190 to 630, more preferably from about 285 to 420, most preferably from about 380 to 420 g/mol. Suitable commercially available materials include for example PEG 400 (ex BDH Chemicals). Mixtures of any of the above described materials may also be used.

The amount of liquid polyethylene glycol (as defined above) in compositions of the invention suitably ranges from 1 to 20%, preferably from 5 to 15%, more preferably from 8 to 12% by total weight liquid polyethylene glycol (as defined above) based on the total weight of the composition.

Product Form and Optional Ingredients

The composition of the invention is typically in the form of a dentifrice. The term "dentifrice" denotes a formulation which are used to clean the surfaces of the oral cavity. The dentifrice is an oral composition that is not intentionally swallowed for purposes of systemic administration of therapeutic agents, but is retained in the oral cavity for a sufficient time to contact substantially all of the dental surfaces and/or mucosal tissues for purposes of oral activity. Preferably the dentifrice is suitable for application with a toothbrush and is rinsed off after use. Preferably the dentifrice is in the form of an extrudable semi-solid such as a cream, paste or gel (or mixture thereof).

A dentifrice composition according to the invention will generally contain further ingredients to enhance performance and/or consumer acceptability such as abrasive cleaning agent and surfactant.

For example, a dentifrice will usually comprise an abrasive cleaning agent in an amount of from 3 to 75% by weight based on the total weight of the dentifrice. Suitable abrasive cleaning agents include particulate abrasive materials such as abrasive silicas, aluminas, calcium carbonates, zirconium silicate, polymethylmethacrylate, dicalcium phosphates, calcium pyrophosphates, hydroxyapatites, trimetaphosphates, insoluble hexametaphosphates and agglomerates and/or mixtures thereof.

Furthermore, a dentifrice will usually contain a surfactant in an amount of from 0.2 to 5% by weight based on the total weight of the dentifrice. Suitable surfactants include anionic surfactants, such as the sodium, magnesium, ammonium or ethanolamine salts of $C_8$ to $C_{18}$ alkyl sulphates (for example sodium lauryl sulphate), $C_8$ to $C_{18}$ alkyl sulphosuccinates (for example dioctyl sodium sulphosuccinate), $C_8$ to $C_{18}$ alkyl sulphoacetates (such as sodium lauryl sulphoacetate), $C_8$ to $C_{18}$ alkyl sarcosinates (such as sodium lauryl sarcosinate), $C_8$ to $C_{18}$ alkyl phosphates (which can optionally comprise up to 10 ethylene oxide and/or propylene oxide units) and sulphated monoglycerides. Other suitable surfactants include nonionic surfactants, such as optionally polyethoxylated fatty acid sorbitan esters, ethoxylated fatty acids, esters of polyethylene glycol, ethoxylates of fatty acid monoglycerides and diglycerides, and ethylene oxide/propylene oxide block polymers. Other suitable surfactants include amphoteric surfactants, such as betaines or sulphobetaines. Mixtures of any of the above described materials may also be used.

Being non-aqueous, the composition of the invention is particularly suitable as a vehicle for oral care actives which may be physically or chemically incompatible with water, or which may function less efficiently in an aqueous environment.

Specific examples of oral care actives which may be included in the compositions of the invention include:

fluoride sources such as sodium fluoride, stannous fluoride, sodium monofluorophosphate, zinc ammonium fluoride, tin ammonium fluoride, calcium fluoride, cobalt ammonium fluoride and mixtures thereof;

plant-derivable antioxidants such as flavonoid, catechin, polyphenol, and tannin compounds and mixtures thereof;

antioxidant vitamins such as tocopherols and/or derivatives thereof, ascorbic acid and/or derivatives thereof and mixtures thereof.

Preferred examples of oral care actives for inclusion in the compositions of the invention include agents for the remineralisation of teeth. The term "remineralisation" in the context of the present invention means the in situ generation of hydroxyapatite on teeth.

A specific example of a suitable agent for the remineralisation of teeth is a mixture of a calcium source and a phosphate source which, when delivered to the teeth results in the in situ generation of hydroxyapatite on teeth.

Illustrative examples of the types of calcium source that may be used in this context (hereinafter termed "remineralising calcium sources") include, for example, calcium phosphate, calcium gluconate, calcium oxide, calcium lactate, calcium glycerophosphate, calcium carbonate, calcium hydroxide, calcium sulphate, calcium carboxymethyl cellulose, calcium alginate, calcium salts of citric acid, calcium silicate and mixtures thereof. Preferably the remineralising calcium source is calcium silicate.

The amount of remineralising calcium source(s) (e.g. calcium silicate) in the composition of the invention typically ranges from 1 to 30%, preferably from 5 to 20% by total weight remineralising calcium source based on the total weight of the oral care composition.

Illustrative examples of the types of phosphate source that may be used in this context (hereinafter termed "remineralising phosphate sources") include, for example, sodium dihydrogen phosphate, disodium hydrogen phosphate, sodium pyrophosphate, tetrasodium pyrophosphate, sodium tripolyphosphate, sodium hexametaphosphate, potassium dihydrogenphosphate, trisodium phosphate, tripotassium phosphate and mixtures thereof. Preferably the remineralising phosphate source is a mixture of trisodium phosphate and sodium dihydrogen phosphate.

The amount of remineralising phosphate source(s) (e.g. trisodium phosphate and sodium dihydrogen phosphate) in the composition of this invention typically ranges from 2 to 15%, preferably from 4 to 10% by total weight remineralising phosphate source based on the total weight of the oral care composition.

Mixtures of any of the above described materials may also be used.

Compositions of the present invention may also contain further optional ingredients customary in the art such as anticaries agents, anticalculus agents, buffers, flavouring agents, sweetening agents, colouring agents, opacifying agents, preservatives, antisensitivity agents, antimicrobial agents and the like.

Process

The invention also provides a process of preparing a non-aqueous oral care composition as defined above, comprising the steps of forming a mixture comprising the thickening agent, the humectant, the liquid polyethylene glycol(s) and the solid polyethylene glycol(s), heating the mixture to a temperature above the melting point of the solid polyethylene glycol(s), and cooling the mixture to form crystals of the solid polyethylene glycol(s).

A preferred process according of the invention comprises the following steps:

(i) heating a mixture of the humectant and the liquid polyethylene glycol(s) to a temperature above the melting point of the solid polyethylene glycol(s) and dispersing the solid polyethylene glycol(s) into the mixture;

(ii) adding powdered ingredients (such as abrasive cleaning agent and/or surfactant) to the mixture so obtained;

(iii) adding the thickening agent to the mixture so obtained, and (iv) cooling the mixture to form crystals of the solid polyethylene glycol(s).

Further optional ingredients (such as the fluoride sources and/or the agents for the remineralisation of teeth, as described above) may suitably be added between steps (i) and (ii).

The invention is further illustrated with reference to the following, non-limiting Example.

Example

The following formulation represents a dentifrice composition according to the invention.

| Ingredient | (% w/w) |
| --- | --- |
| Glycerol (99.5% a.i.) | 55.14 |
| PEG 400 (ex BDH Chemicals) | 10.5 |
| Flavour | 1.0 |
| Trisodium phosphate | 3.8 |
| Calcium silicate | 15.0 |
| Sodium monofluorophosphate | 1.11 |
| Sodium saccharin | 0.2 |
| CARBOPOL ® 974P NF Polymer, (ex Lubrizol Advanced Materials, Inc.) | 0.3 |
| Monosodium dihydrogen phosphate | 3.2 |
| Polyglykol ® 3000 (ex Clariant) | 1.75 |
| Sodium lauryl sulphate (powdered) | 2.0 |
| Abrasive silica (powdered) | 6.0 |

The formulation was prepared as follows:

(i) Heat the glycerol and the PEG 400 to 60° C., and disperse the Polyglykol® 3000;

(ii) Add the trisodium phosphate, monosodium dihydrogen phosphate, sodium monofluorophosphate and sodium saccharin and mix until lump free, keeping the temperature at 60° C.;

(iii) Add the mixture to a Fryma®DT10 mixer and mix for 5 minutes;

(iv) Draw the calcium silicate slowly into the mixture and mix for 10 minutes;

(v) Pre-mix the sodium lauryl sulphate and abrasive silica, draw in to the mixture and mix for 10 minutes;

(vi) Add the CARBOPOL® 974P NF Polymer and mix for 5 minutes;

(vii) Cool the mixture to 30° C., add flavour and mix to disperse.

The invention claimed is:

1. A non-aqueous oral care composition, comprising:
   a liquid continuous phase comprising:
      a thickening agent,
      a humectant, and
      one or more liquid polyethylene glycols having a melting point below 25° C.;
   wherein the thickening agent comprises a carboxyvinyl polymer with a molecular weight of at least 750,000 g/mol;
   wherein the liquid continuous phase comprises crystals of one or more solid polyethylene glycols;
   wherein the liquid polyethylene glycols have an average molecular weight of 285 to 420;
   wherein the liquid polyethylene glycols are present in an amount of 5 to 15 wt % of the non-aqueous oral care composition;
   wherein the solid polyethylene glycols are present in an amount of 0.1 to 5 wt % of the non-aqueous oral care composition;
   wherein water is present in an amount of no greater than 3 wt % of the non-aqueous oral care composition; and
   wherein each of the one or more solid polyethylene glycols has a general formula $H(OCH_2CH_2)_n OH$, where n is a number of repeating oxyethylene units, and wherein an average value of n ranges from 60 to 150.

2. The composition according to claim 1, wherein the thickening agent comprises a carboxyvinyl polymer selected from homopolymers of acrylic acid cross-linked with allyl ethers of sucrose or pentaerythritol; and homopolymers of acrylic acid cross-linked with divinyl glycol.

3. The composition according to claim 1, wherein the humectant is one or more organic polyols having 3 or more hydroxyl groups in the molecule.

4. The composition according to claim 1, wherein the average value of n ranges from 60 to 75.

5. The composition according to claim 1, wherein the liquid polyethylene glycol has a melting point ranging from −15 to 8° C.

6. The composition according to claim 1, wherein the liquid polyethylene glycol has the general formula $H(OCH_2CH_2)_n OH$, where n is the number of repeating oxyethylene units, and the average value of n ranges from 6 to 8.

7. The oral care composition according to claim 1, which is in the form of a dentifrice comprising an abrasive cleaning agent in an amount of from 3 to 75% by weight based on the total weight of the dentifrice, and a surfactant in an amount of from 0.2 to 5% by weight based on the total weight of the dentifrice.

8. The oral care composition according to claim 1, which further comprises a mixture of a calcium source and a phosphate source.

9. The oral care composition according to claim 8, in which the calcium source is calcium silicate and the phosphate source is a mixture of trisodium phosphate and sodium dihydrogen phosphate.

10. The oral care composition according to claim 1, which further comprises one or more oral care actives selected from fluoride sources, plant-derivable antioxidants and antioxidant vitamins.

11. A process of preparing the non-aqueous oral care composition according to claim 1, comprising the steps of
   forming a mixture comprising the thickening agent, the humectant, the one or more liquid polyethylene glycols and the one or more solid polyethylene glycols;
   heating the mixture to a temperature above the melting point of the one or more solid polyethylene glycols; and
   cooling the mixture to form crystals of the one or more solid polyethylene glycols.

* * * * *